US010699814B2

(12) United States Patent
Yui et al.

(10) Patent No.: US 10,699,814 B2
(45) Date of Patent: Jun. 30, 2020

(54) REGIONAL MEDICAL COOPERATION SYSTEM

(71) Applicant: Hitachi, Ltd., Chiyoda-ku, Tokyo (JP)

(72) Inventors: Shuntaro Yui, Tokyo (JP); Jumpei Sato, Tokyo (JP); Kunihiko Kido, Tokyo (JP); Takuya Kamiyama, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1123 days.

(21) Appl. No.: 14/653,659

(22) PCT Filed: Dec. 21, 2012

(86) PCT No.: PCT/JP2012/083194
§ 371 (c)(1),
(2) Date: Jun. 18, 2015

(87) PCT Pub. No.: WO2014/097466
PCT Pub. Date: Jun. 26, 2014

(65) Prior Publication Data
US 2015/0310184 A1 Oct. 29, 2015

(51) Int. Cl.
*G16H 80/00* (2018.01)
*G16H 40/20* (2018.01)
(Continued)

(52) U.S. Cl.
CPC ............ *G16H 80/00* (2018.01); *G06Q 10/10* (2013.01); *G06Q 50/22* (2013.01); *G16H 40/20* (2018.01); *G16H 50/30* (2018.01)

(58) Field of Classification Search
CPC ...... G06F 19/325; G06Q 50/22; G06Q 50/24; G06Q 10/10; G16H 40/20; G16H 50/30;
(Continued)

(56) References Cited

U.S. PATENT DOCUMENTS

2003/0167187 A1* 9/2003 Bua ..................... G06Q 50/22
705/2
2006/0167721 A1* 7/2006 Bernard ................ G06Q 50/22
705/2
(Continued)

FOREIGN PATENT DOCUMENTS

JP 2005-122380 A 5/2005
JP 2005-258854 A 9/2005
(Continued)

OTHER PUBLICATIONS

International Search Report (PCT/ISA/210) dated Feb. 5, 2013, with English translation (Four (4) pages).
(Continued)

*Primary Examiner* — Joseph D Burgess
(74) *Attorney, Agent, or Firm* — Crowell & Moring LLP

(57) ABSTRACT

The task is to provide a system which supports smooth patient referral from a referral source medical institution to a referral destination medical institution and which particularly prevents readmission due to cases that are difficult to determine simply based on patient attributes or due to the quality of medical services. To achieve this task, a referral difficult degree calculation unit calculates a referral difficulty degree which quantifies the risk that a patient cannot be discharged because a referral destination cannot be found, in consideration of a readmission risk calculated by a readmission risk calculation unit, the geographical distance between the patient and the referral destination medical institution, the total number of patients accepted, and the number of beds available. This referral difficulty degree is outputted to an output unit of the referral source medical institution or the referral destination medical institution.

13 Claims, 22 Drawing Sheets

(51) Int. Cl.
*G16H 50/30* (2018.01)
*G06Q 50/22* (2018.01)
*G06Q 10/10* (2012.01)

(58) Field of Classification Search
CPC ........ G16H 10/60; G16H 50/70; G16H 50/20;
G16H 50/50; G16H 15/00; G16H 10/20;
G16H 10/40; G16H 40/63; G16H 80/00;
G16H 40/40; G16H 20/10; G16H 20/70;
G16H 40/67
See application file for complete search history.

(56) References Cited

U.S. PATENT DOCUMENTS

2011/0295622 A1* 12/2011 Farooq .................. G06Q 10/10
705/3
2013/0096942 A1* 4/2013 Bowles ................. G06Q 50/22
705/2

FOREIGN PATENT DOCUMENTS

| JP | 2007-94943 A | 4/2007 |
| JP | 2010-9086 A | 1/2010 |
| JP | 2011-209851 A | 10/2011 |

OTHER PUBLICATIONS

Otsubo et al., "Readmission Rate for Health Care Delivery System Assessment", Department of Healthcare Economics and Quality Management, Kyoto University, vol. 67, No. 1, pp. 62-66, 2012, with English Abstract (Five (5) pages).

\* cited by examiner

[FIG. 1]
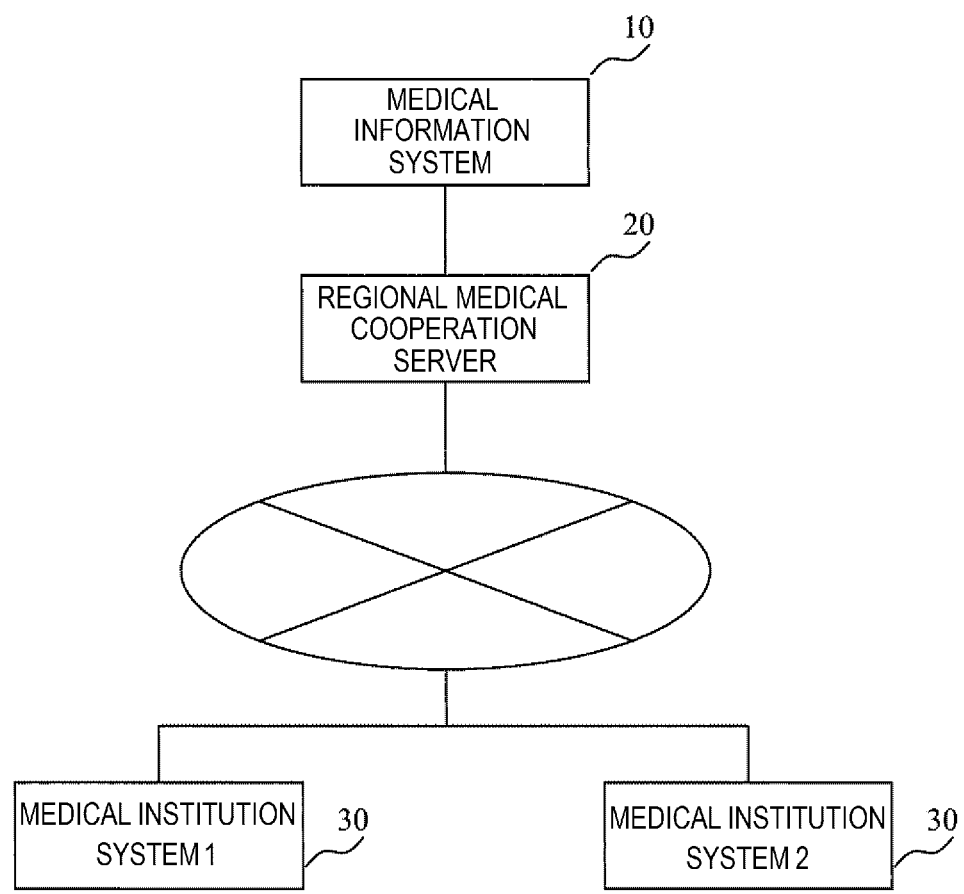

[FIG. 2]
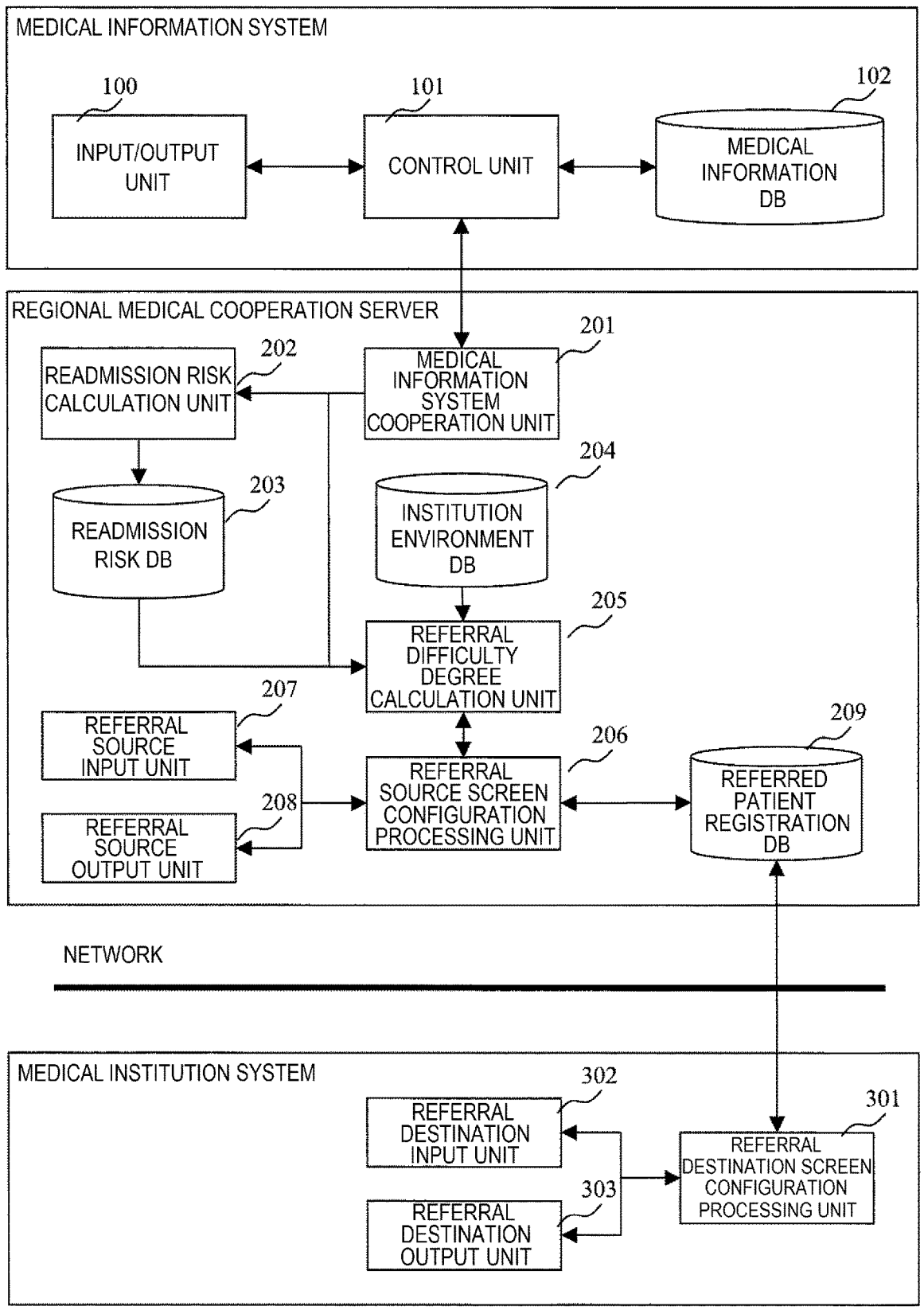

[FIG. 3]
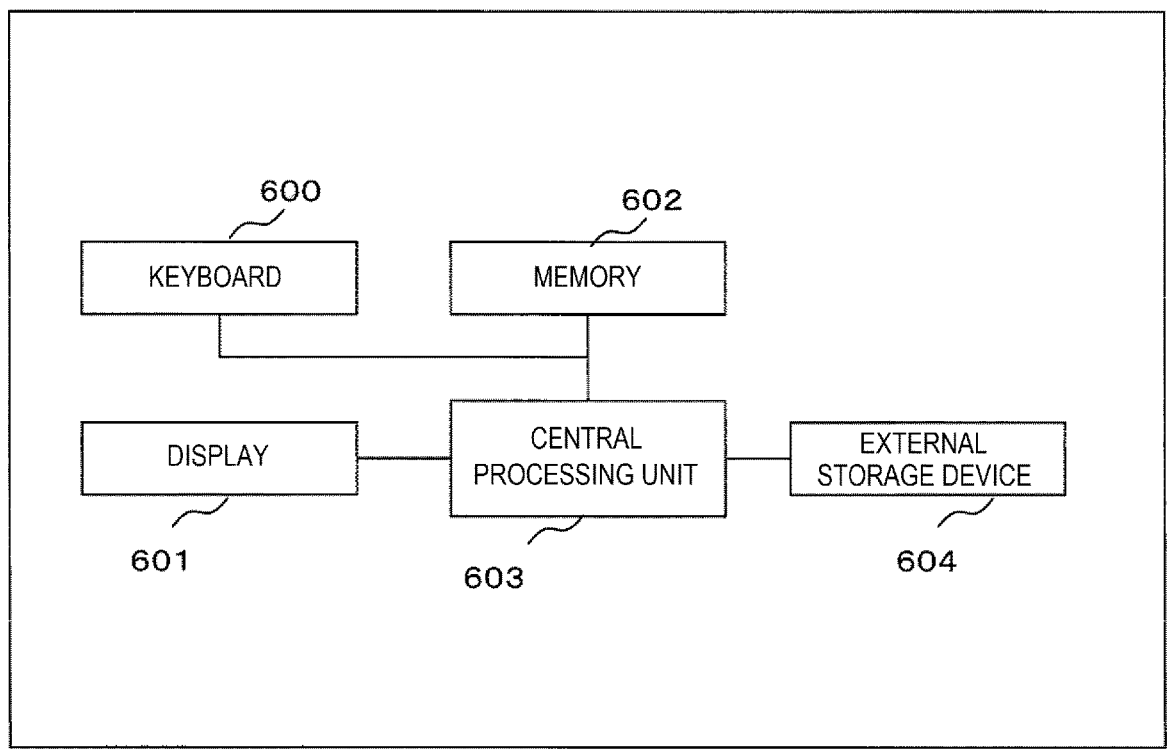

[FIG. 4]
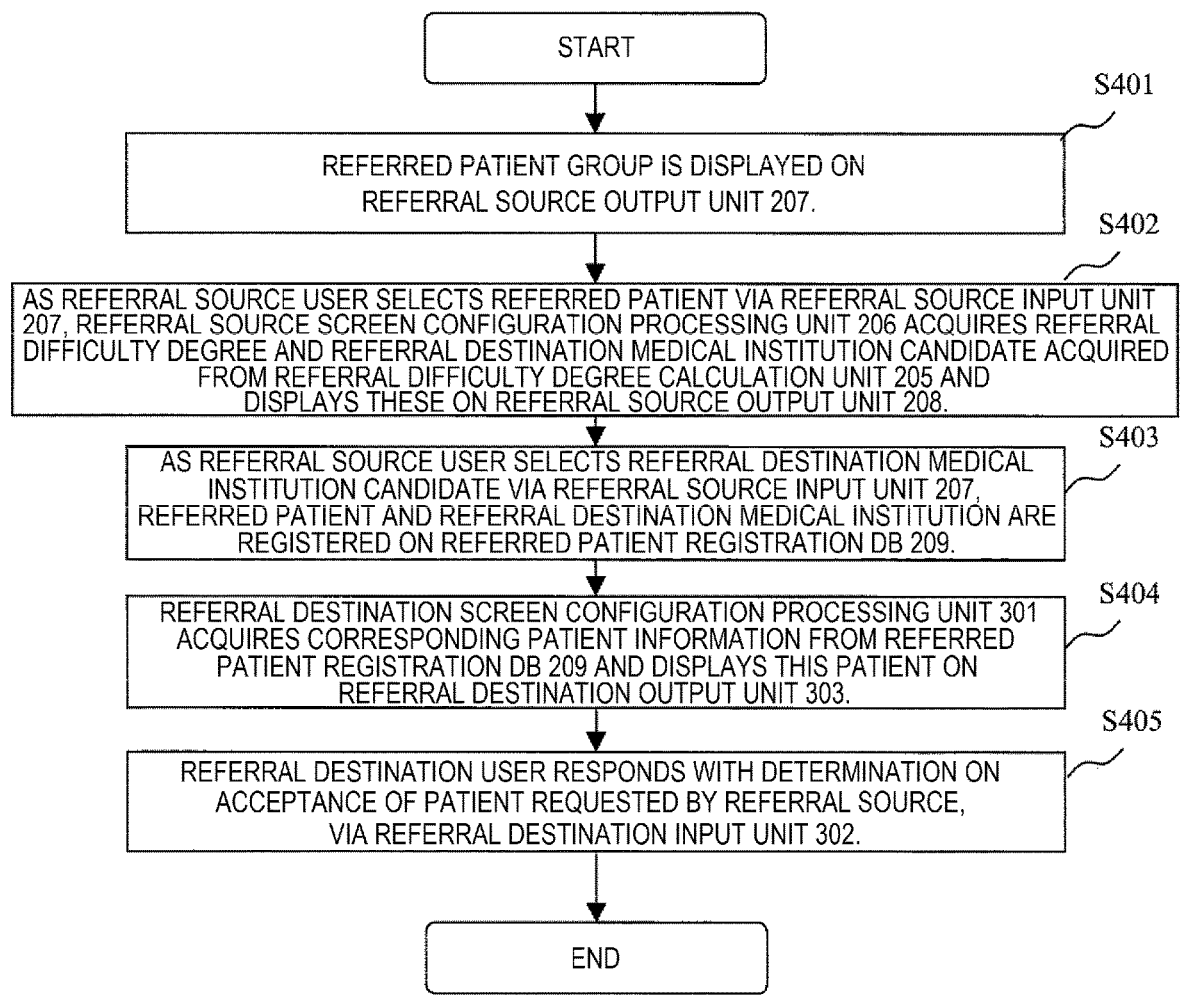

[FIG. 5]

REFERRAL SOURCE OUTPUT SCREEN

501
- ● P0 : ISCHEMIC HEART DISEASE
- ○ P1 : ISCHEMIC HEART DISEASE
- ○ P2 : DIABETES
- ...

504 REFERRAL REQUEST

502 CONDITION SETTING SECTION

| | | |
|---|---|---|
| READMISSION RISK | ▼ None | OR BELOW |
| GEOGRAPHICAL CONDITION | ▼ None | MINUTES OR BELOW |
| NUMBER OF PATIENTS TREATED | ▼ 100 | CASES OR ABOVE |
| REFERRAL DIFFICULTY DEGREE | ▼ 3.0 | OR BELOW |

REFERRAL DESTINATION MEDICAL INSTITUTION CANDIDATE

503

| | HOSPITAL NAME | RISK | | TOTAL NUMBER OF PATIENTS ACCEPTED | REFERRAL DIFFICULTY DEGREE |
| | | RE-ADMISSION RISK | GEO-GRAPHICAL CONDITION | | |
|---|---|---|---|---|---|
| ● | A HOSPITAL | 20 | 20 MINUTES ON FOOT | 100 CASES | 3.0 |
| ○ | C HOSPITAL | 30 | 10 MINUTES ON FOOT | 200 CASES | 2.0 |
| ○ | B HOSPITAL | 10 | 30 MINUTES ON FOOT | 200 CASES | 1.0 |

[FIG. 6]

REFERRED PATIENT REGISTRATION TABLE

| INSTITUTION NAME | PATIENT NAME | DISEASE NAME |
|---|---|---|
| B INSTITUTION | P1 | ISCHEMIC HEART DISEASE |
| C INSTITUTION | P2 | DIABETES |
| A INSTITUTION | P0 | ISCHEMIC HEART DISEASE |
| ... | ... | ... |

[FIG. 7]
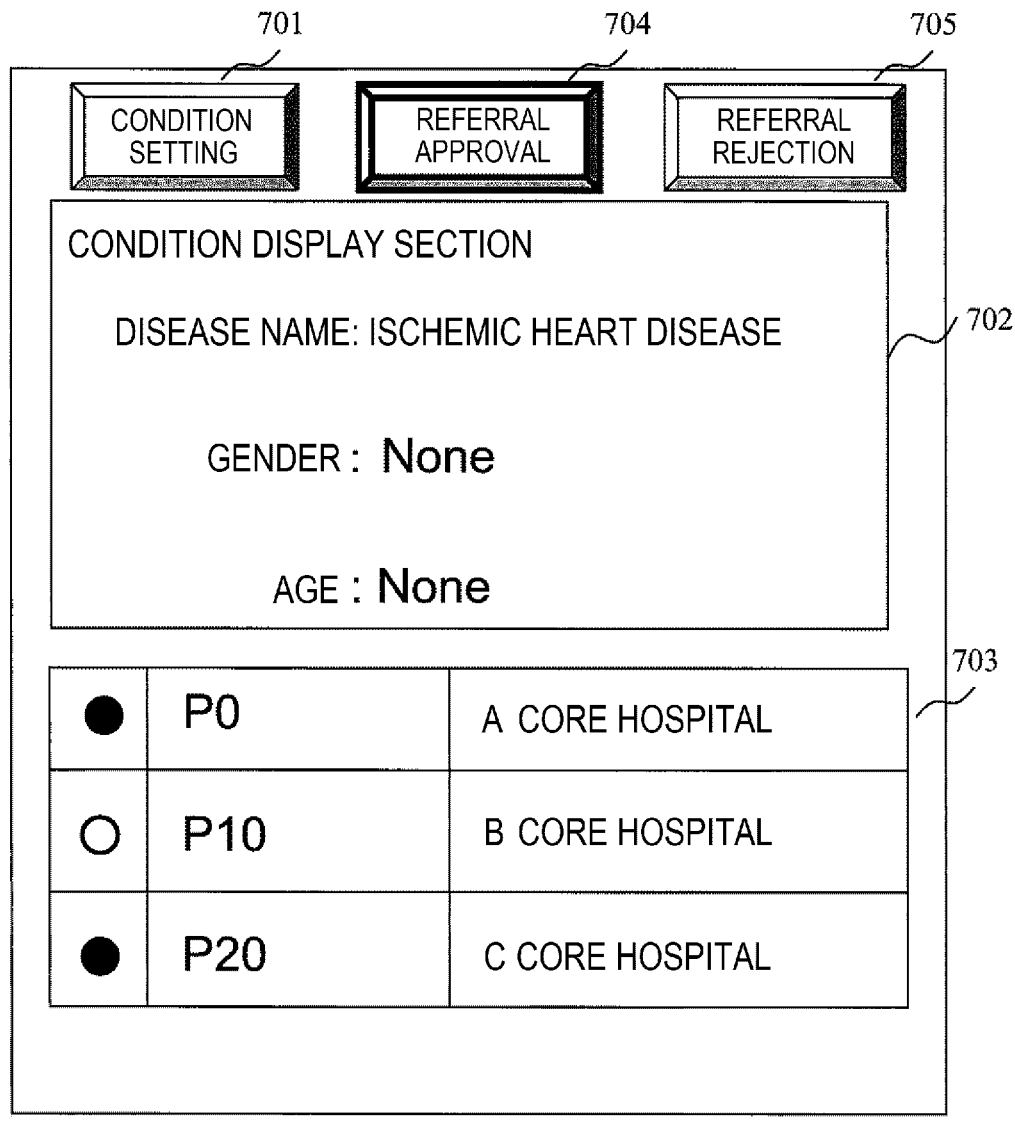

[FIG. 8]

INSTITUTION INFORMATION TABLE

| INSTITUTION NAME | POSTCODE | NUMBER OF BEDS | NUMBER OF BEDS AVAILABLE |
|---|---|---|---|
| A INSTITUTION | 111-5212 | 500 | 10 |
| B INSTITUTION | 254-9856 | 700 | 100 |
| C INSTITUTION | 352-9768 | 300 | 5 |
| ... | ... | ... | ... |

DISEASE BASIC INFORMATION TABLE

| INSTITUTION NAME | DISEASE NAME | NUMBER OF DOCTORS | TOTAL NUMBER OF PATIENTS ACCEPTED |
|---|---|---|---|
| A INSTITUTION | ISCHEMIC HEART DISEASE | 20 | 500 |
| A INSTITUTION | HEPATOMA | 20 | 200 |
| A INSTITUTION | DIABETES | 10 | 150 |
| B INSTITUTION | ISCHEMIC HEART DISEASE | 20 | 500 |
| B INSTITUTION | HEPATOMA | 20 | 200 |
| B INSTITUTION | DIABETES | 10 | 300 |
| C INSTITUTION | ISCHEMIC HEART DISEASE | 20 | 500 |
| C INSTITUTION | HEPATOMA | 20 | 200 |
| C INSTITUTION | DIABETES | 3 | 20 |
| ... | ... | ... | ... |

[FIG. 9]
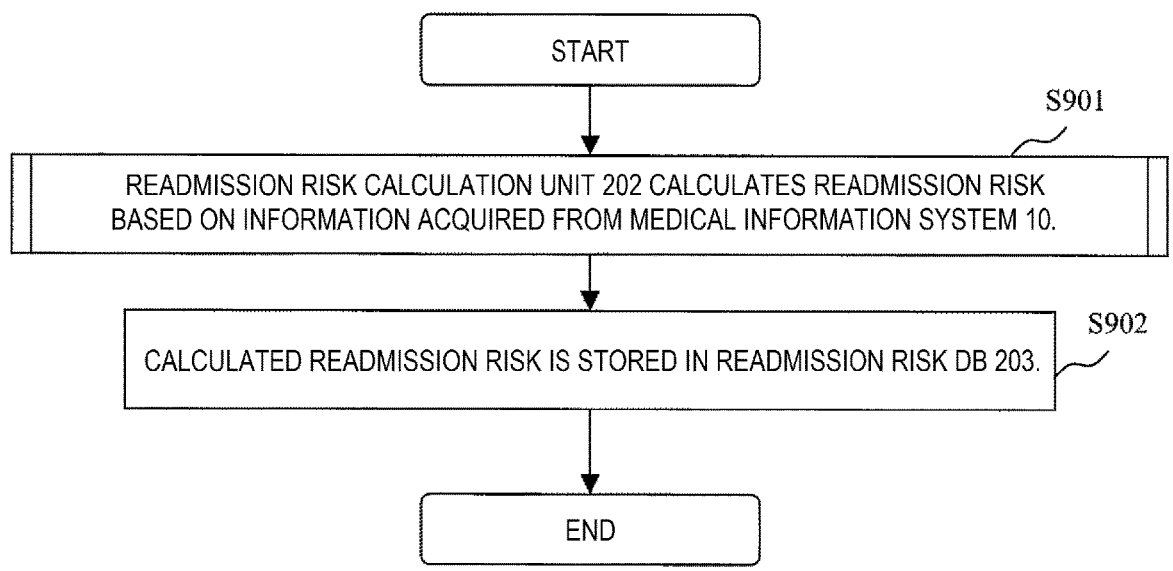

[FIG. 10]

PATIENT BASIC INFORMATION TABLE

| PATIENT CODE | GENDER | DATE OF BIRTH | POST CODE |
|---|---|---|---|
| P0 | MALE | 1950/5/1 | 111-5214 |
| P1 | FEMALE | 1940/5/1 | 800-6842 |
| P2 | MALE | 1948/8/1 | 254-9876 |
| P3 | MALE | 1951/3/3 | 352-9768 |
| ... | ... | ... | ... |

PATIENT ADMISSION BASIC INFORMATION TABLE

| PATIENT CODE | DATE OF ADMISSION | DATE OF DISCHARGE | DISEASE NAME | REFERRAL DESTINATION MEDICAL INSTITUTION | RE-ADMISSION FLAG |
|---|---|---|---|---|---|
| P0 | 1/10 | 1/14 | ISCHEMIC HEART DISEASE | A INSTITUTION | 0 |
| P1 | 2/10 | 2/20 | HEPATOMA | A INSTITUTION | 0 |
| P1 | 3/14 | 3/26 | ISCHEMIC HEART DISEASE | B INSTITUTION | 1 |
| P2 | 4/15 | 4/26 | HEPATOMA | B INSTITUTION | 1 |
| P3 | 5/1 | - | HEPATOMA | - | - |
| ... | ... | ... | ... | ... | ... |

[FIG. 11]

CONDUCTED PRACTICE INFORMATION TABLE

| PATIENT CODE | DATE OF PRACTICE | MEDICAL PRACTICE | PRACTICE CODE |
|---|---|---|---|
| P0 | 1/10 | ORIENTATION | 001 |
| P0 | 1/11 | BLOOD PRESSURE CHECK | 002 |
| P0 | 1/11 | BODY TEMPERATURE CHECK | 003 |
| P0 | 1/12 | CATHETER INSERTION | 004 |
| P0 | 1/12 | HEMORRHAGE CHECK | 005 |
| P1 | 2/10 | ULTRASOUND | 001 |
| P1 | 2/11 | TACE | 002 |
| P1 | 2/11 | LIPIODOL | 003 |
| P1 | 2/11 | REST GUIDANCE | 004 |
| P2 | 4/15 | ORIENTATION | 001 |
| ... | ... | ... | ... |

[FIG. 12]

READMISSION RISK TABLE

| CATEGORY TYPE | CATEGORY VALUE | CATEGORY SCORE (DISCRIMINANT COEFFICIENT) |
|---|---|---|
| GENDER | MALE | 0.01 |
| GENDER | FEMALE | −0.01 |
| AGE | UNDER 6 YEARS OLD | 0.01 |
| AGE | 6 YEARS OLD TO UNDER 60 YEARS OLD | −0.03 |
| AGE | 60 YEARS OLD AND ABOVE | 0.02 |
| DISEASE NAME | ISCHEMIC HEART DISEASE | 0.06 |
| DISEASE NAME | HEPATOMA | 0.04 |
| DISEASE NAME | DIABETES | 0.03 |
| ... | ... | ... |

[FIG. 13]
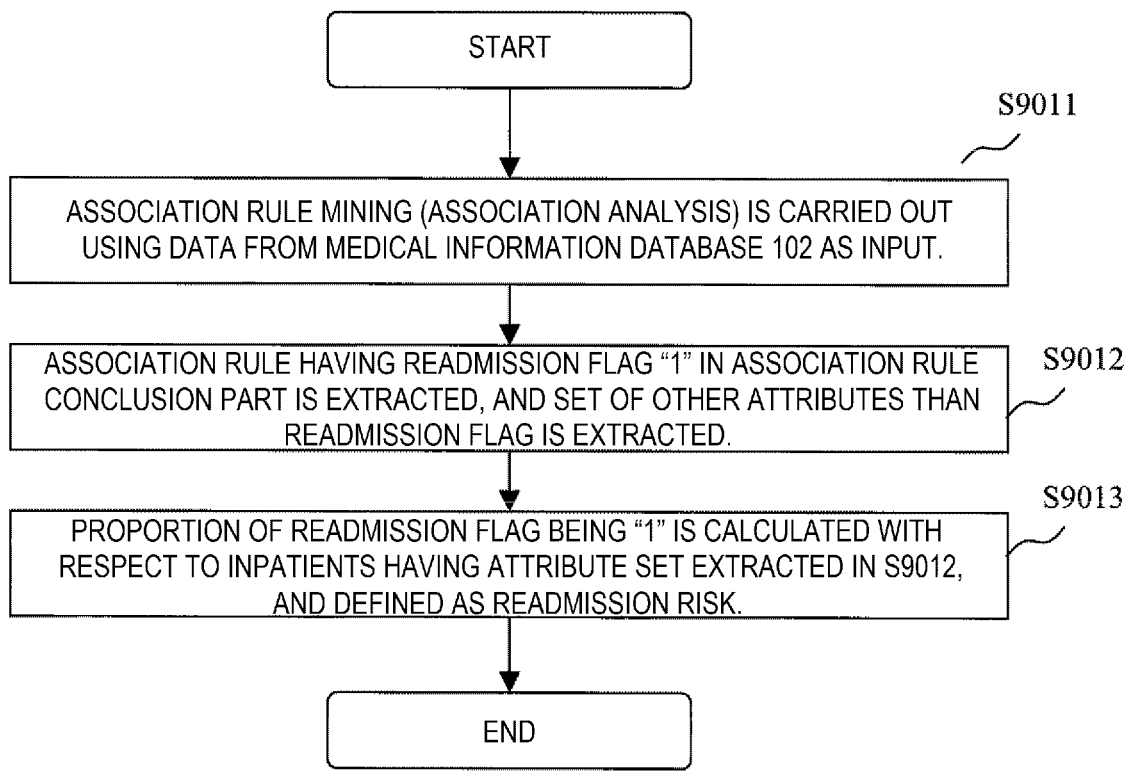

[FIG. 14]

READMISSION RISK TABLE

| GENDER | PRACTICE (TECHNIQUE) | PRACTICE (OTHER) | SEASON | AGE | DISEASE NAME | REFERRAL DESTINATION MEDICAL INSTITUTION NAME | RISK |
|---|---|---|---|---|---|---|---|
| – | – | – | WINTER | 65 YEARS OLD OR ABOVE | ISCHEMIC HEART DISEASE | B INSTITUTION | 30 |
| – | – | – | WINTER | 65 YEARS OLD OR ABOVE | ISCHEMIC HEART DISEASE | C INSTITUTION | 20 |
| – | – | – | WINTER | 65 YEARS OLD OR ABOVE | ISCHEMIC HEART DISEASE | A INSTITUTION | 10 |
| MALE | RFA | – | – | – | HEPATOCELLULAR CARCINOMA | B INSTITUTION | 10 |
| – | TACE | LIPIODOL | – | – | HEPATOCELLULAR CARCINOMA | A INSTITUTION | 5 |
| – | TACE | LIPIODOL | – | – | HEPATOCELLULAR CARCINOMA | B INSTITUTION | 10 |
| – | TACE | LIPIODOL | – | – | HEPATOCELLULAR CARCINOMA | C INSTITUTION | 15 |
| – | HEPATECTOMY | – | – | – | HEPATOCELLULAR CARCINOMA | A INSTITUTION | 25 |
| – | HEPATECTOMY | – | – | – | HEPATOCELLULAR CARCINOMA | B INSTITUTION | 30 |
| – | HEPATECTOMY | – | – | – | HEPATOCELLULAR CARCINOMA | C INSTITUTION | 35 |
| MALE | – | – | – | 20 TO 65 YEARS OLD | DIABETES | B INSTITUTION | 30 |
| ... | ... | ... | ... | ... | ... | ... | ... |

[FIG. 15]
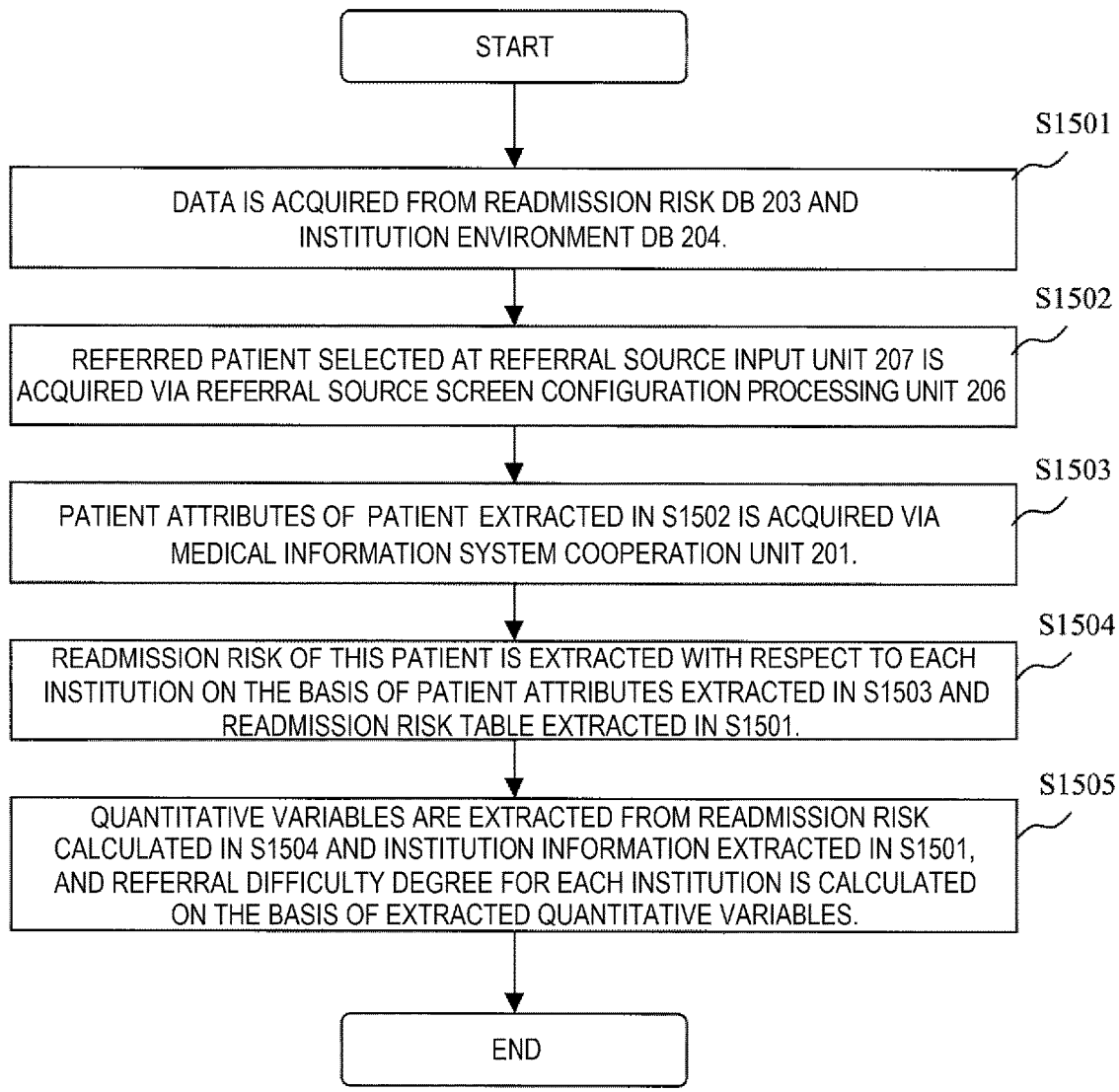

[FIG. 16]
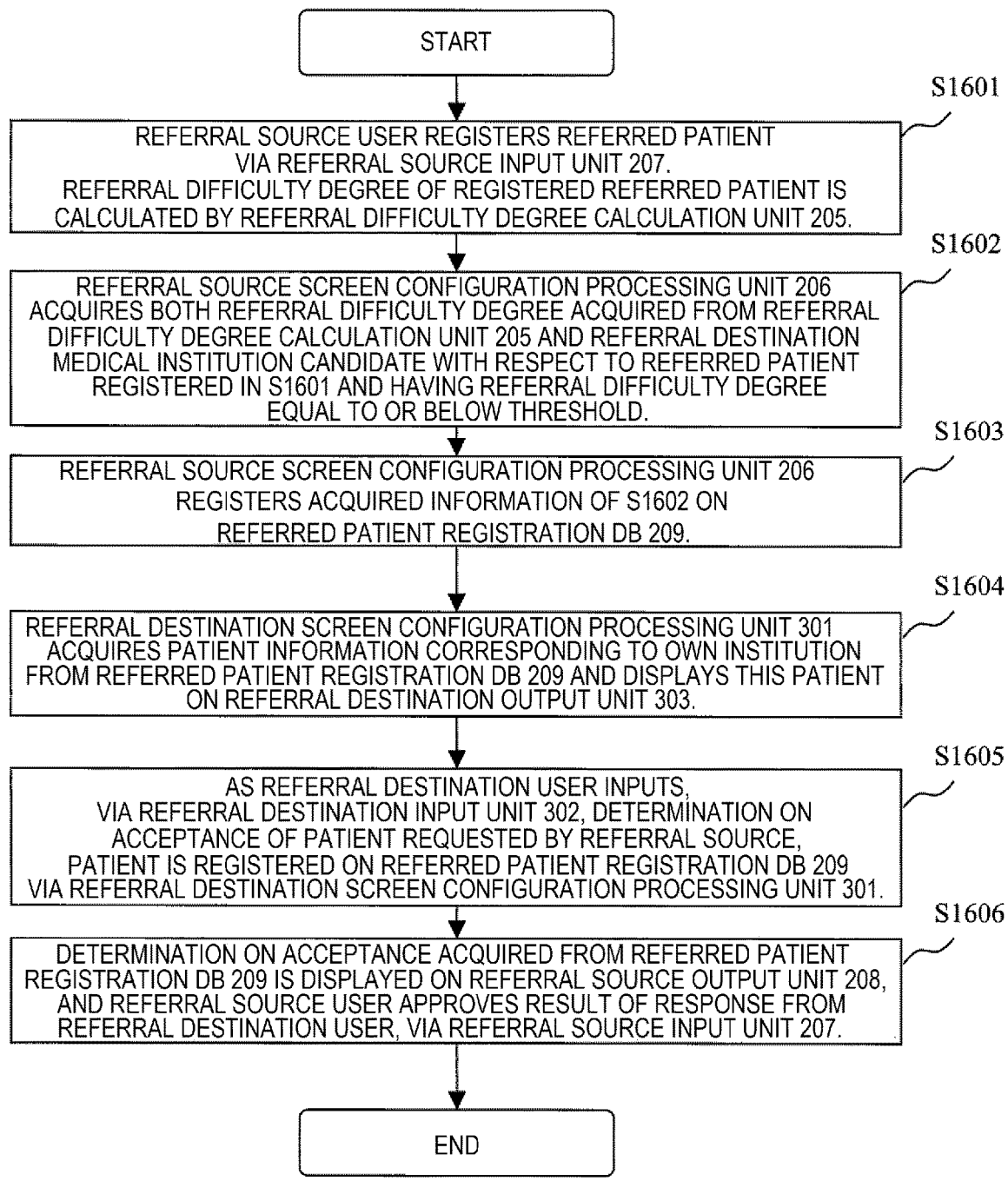

[FIG. 17]

REFERRED PATIENT REGISTRATION TABLE

| INSTITUTION NAME | PATIENT NAME | DISEASE NAME | RE-ADMISSION RISK | GEO-GRAPHICAL CONDITION | REFERRAL DIFFICULTY DEGREE | REFERRAL DESTINATION ACCEPTANCE AVAILABILITY |
|---|---|---|---|---|---|---|
| B INSTITUTION | P1 | ISCHEMIC HEART DISEASE | 20% | 20 MINUTES ON FOOT | 3.0 | NO REPLY |
| C INSTITUTION | P2 | DIABETES | 10% | 30 MINUTES ON FOOT | 1.0 | UNAVAILABLE |
| A INSTITUTION | P0 | ISCHEMIC HEART DISEASE | 30% | 10 MINUTES ON FOOT | 2.0 | AVAILABLE |
| ... | ... | ... | ... | ... | ... | ... |

[FIG. 18]
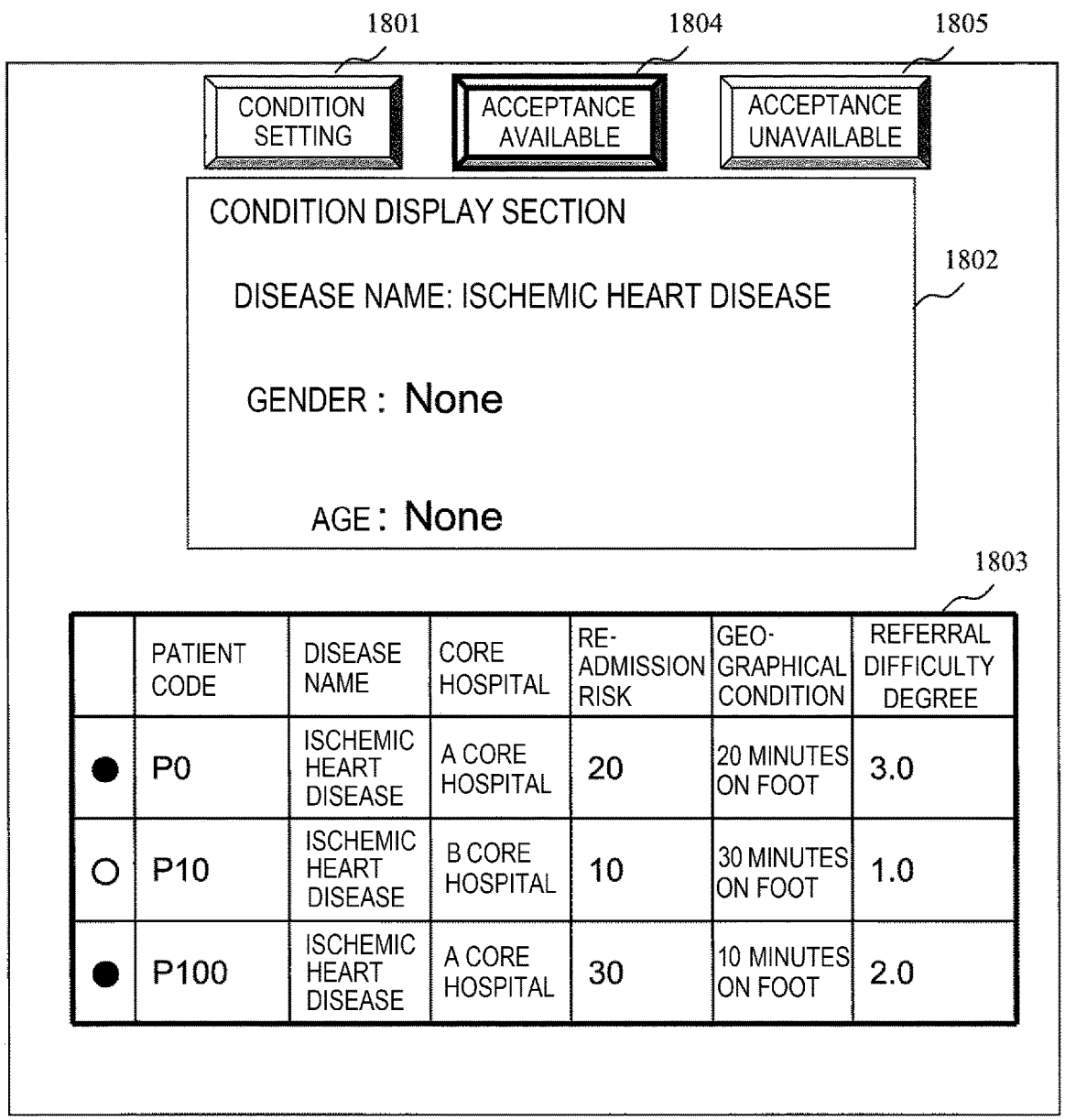

[FIG. 19]
REFERRAL SOURCE OUTPUT SCREEN
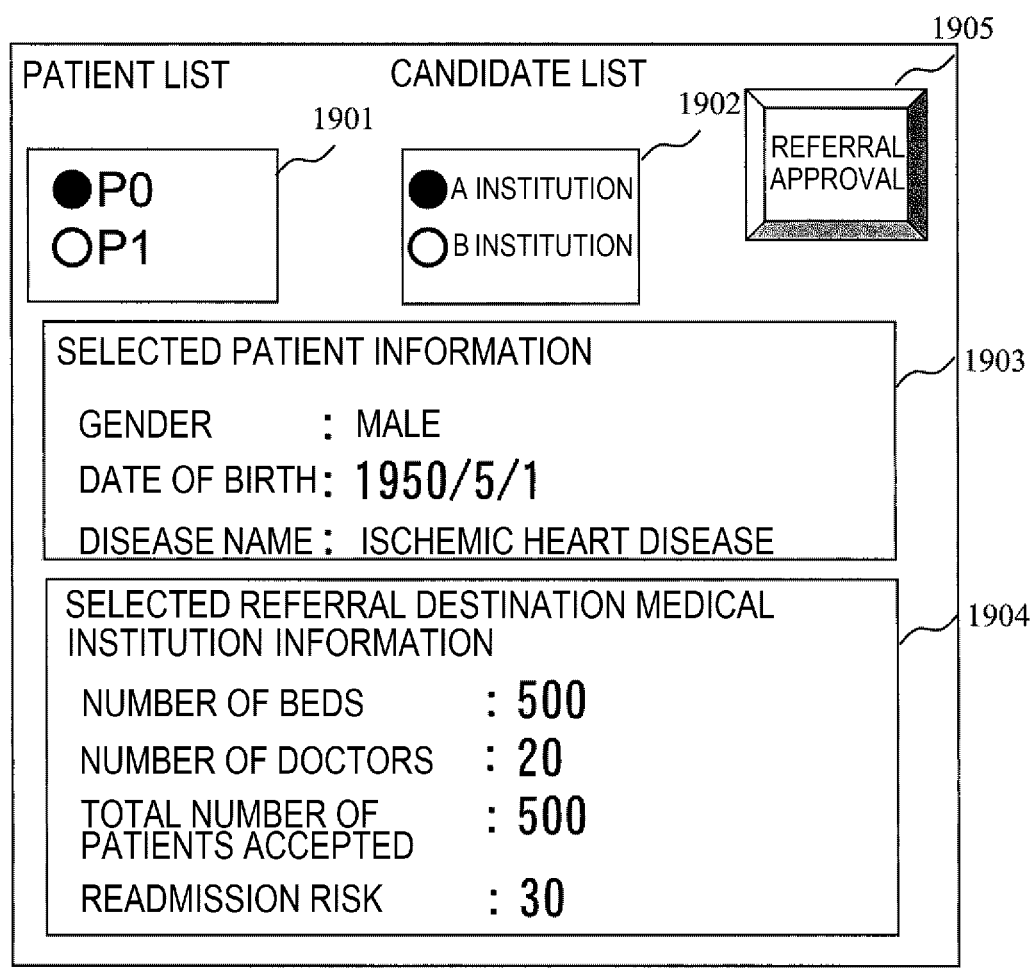

[FIG. 20]
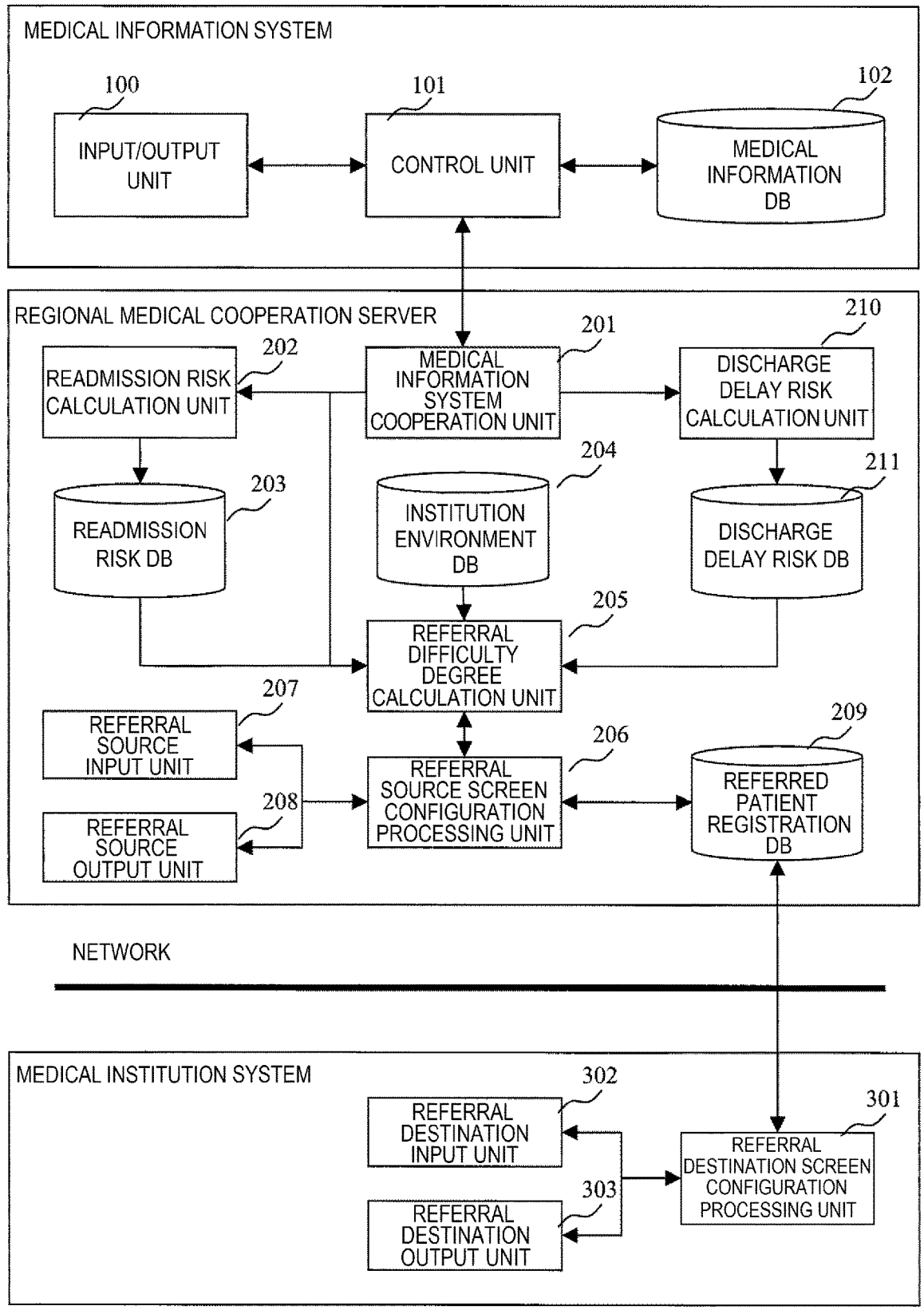

[FIG. 21]
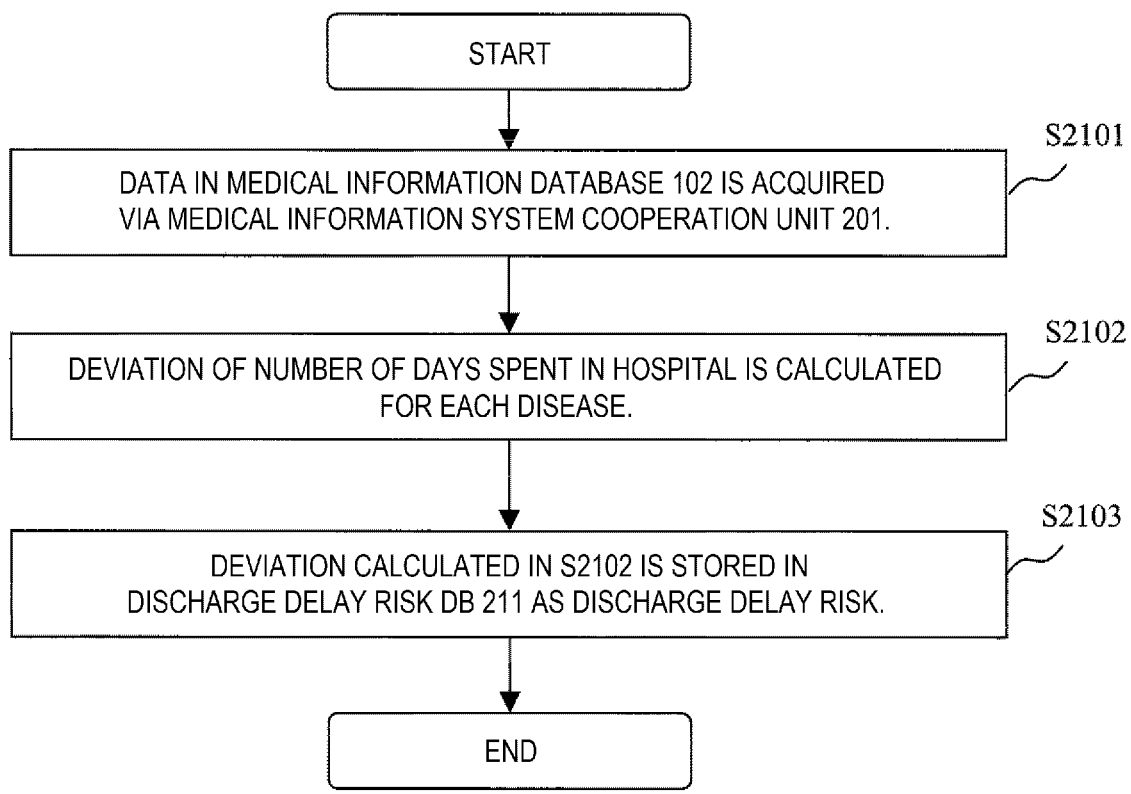

[FIG. 22]
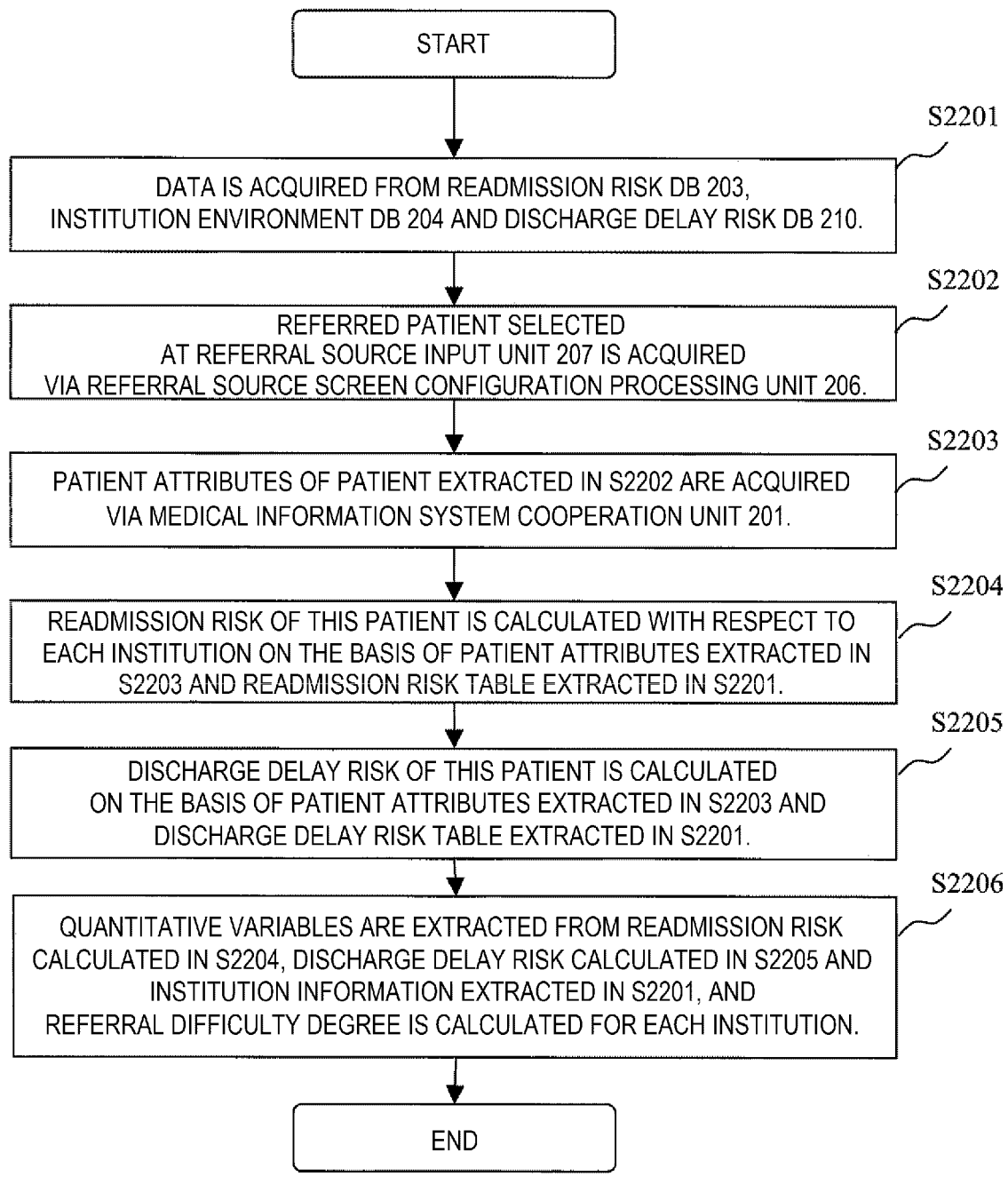

REGIONAL MEDICAL COOPERATION SYSTEM

TECHNICAL FIELD

The present invention relates to a hospital information system technique in the field of medical services and particularly a cooperation system between hospitals for regional medical services.

BACKGROUND ART

As a result of patients' preference for large hospitals and specialists, there is a tendency for patients to concentrate constantly at medical institutions in the secondary medical area and the tertiary medical area. Also, patients who need long-term medical care including home care are increasing because of changes in disease patterns such as lifestyle-related illness. Therefore, there is a need to proceed with the division of functions of medical institutions and further promote regional medical cooperation structures. To this end, it is desired that a regional network should be constructed between acute hospitals and backup hospitals so as to construct an environment where cooperation can be made smoothly for patients.

PTL 1 is a system in which, with reference to a medical cooperation database, a backup hospital (referral destination medical institution) that is suitable as a referral destination for a patient of an acute hospital (referral source medical institution) is selected and referred to. Conditions of selection include patient's condition, available hospital ward, medication, institution, medical treatment fee, region of location, number of specialists, presence/absence of examination equipment and facilities, and the like.

CITATION LIST

Patent Literature

PTL 1: JP-A-2005-258854

SUMMARY OF INVENTION

Technical Problem

As described above, as a conventional regional medical cooperation system, there is a system in which, when a patient is referred to a referral destination medical institution from a referral source medical institution, patient information is shared and the referral destination medical institution is searched for on the basis of the location, symptoms and the like, thus realizing interactive matching (management of acceptance request and permission) between the referral source medical institution and the referral destination medical institution. However, there is a problem that, in the referral of the patient, the patient cannot be discharged from the hospital because no referral destination is found. There is referral difficulty (with a disease for which it is difficult to predict the date of discharge, an advanced bed control technique is needed and it is difficult to accept a referral destination) due to cases where it is difficult to make a decision simply based on patient attributes, for example, where the patient is readmitted as the conditions worsen even if a referral destination is found, or the like. Therefore, solving this problem is a task.

In the case of the foregoing PTL 1, there is a system for searching for a hospital that matches search conditions. However, the quality of medical services such as readmission is not taken into account.

Thus, to realize smooth regional medical cooperation, it is difficult to achieve sufficient effects with the disclosed conventional technique.

Solution to Problem

To solve the above problem, a regional medical cooperation system for supporting patient referral to a referral destination medical institution from a referral source medical institution in regional medical cooperation is provided, the regional medical cooperation system including a medical information system, a regional medical cooperation server at the referral source medical institution, and a medical institution system at the referral destination medical institution, wherein the medical information system has a medical information database which stores medical information including patient information, and wherein the regional medical cooperation server has a medical information system cooperation unit which acquires the medical information stored in the medical information database, a readmission risk calculation unit which calculates a readmission risk that is a risk of being readmitted to the referral source medical institution from the referral destination medical institution on the basis of the medical information acquired from the medical information system cooperation unit, a server referred patient input unit which accepts an input of a first referred patient, and a server output unit which calculates and displays on a screen a referral destination medical institution and a first readmission risk corresponding to the first referred patient.

Advantageous Effect of Invention

By determining the risk of the patient referral in advance, including the readmission risk, which is the risk of being readmitted to the referral source medical institution from the referral destination medical institution, it is possible to improve the patient referral including reduction in the burden on the patient, and realize promotion of a regional medical cooperation structure required by an increase in the number of referred patients. Thus, the turnover of patients rises, contributing to hospital management.

BRIEF DESCRIPTION OF DRAWINGS

FIG. 1 is a schematic view of the configuration of a regional medical cooperation system according to the invention.

FIG. 2 is a first configuration view of the regional medical cooperation system according to the invention.

FIG. 3 is a view of the hardware configuration of the regional medical cooperation system according to the invention.

FIG. 4 is a first flowchart showing a flow of processing in the regional medical cooperation system according to the invention.

FIG. 5 is a first example showing a screen at a referral source medical institution in the regional medical cooperation system according to the invention.

FIG. 6 is a first view showing a referred patient registration database in the regional medical cooperation system according to the invention.

FIG. 7 is a first example showing a screen at a referral destination medical institution in the regional medical cooperation system according to the invention.

FIG. 8 is a view showing an institution environment database in the regional medical cooperation system according to the invention.

FIG. 9 is a first flowchart showing a flow of processing in a readmission risk calculation unit in the regional medical cooperation system according to the invention.

FIG. 10 is a first view showing a medical information database in the regional medical cooperation system according to the invention.

FIG. 11 is a second view showing the medical information database in the regional medical cooperation system according to the invention.

FIG. 12 is a first view showing a readmission risk database in the regional medical cooperation system according to the invention.

FIG. 13 is a second flowchart showing a flow of processing in the readmission risk calculation unit in the regional medical cooperation system according to the invention.

FIG. 14 is a second view showing the readmission risk database in the regional medical cooperation system according to the invention.

FIG. 15 is a first flowchart showing a flow of processing in a referral difficulty degree calculation unit in the regional medical cooperation system according to the invention.

FIG. 16 is a second flowchart showing a flow of processing in the regional medical cooperation system according to the invention.

FIG. 17 is a second view showing the referred patient registration database in the regional medical cooperation system according to the invention.

FIG. 18 is a second example showing the screen at the referral destination medical institution in the regional medical cooperation system according to the invention.

FIG. 19 is a second example showing the screen at the referral source medical institution in the regional medical cooperation system according to the invention.

FIG. 20 is a second configuration view of the regional medical cooperation system according to the invention.

FIG. 21 is a flowchart showing a flow of processing in a discharge delay risk calculation unit in the regional medical cooperation system according to the invention.

FIG. 22 is a second flowchart showing a flow of processing in the referral difficulty degree calculation unit in the regional medical cooperation system according to the invention.

DESCRIPTION OF EMBODIMENTS

Hereinafter, the best mode for carrying out the invention will be described.

Example 1

FIG. 1 is a schematic view of the configuration of a regional medical cooperation system according to the invention. The regional medical cooperation system shown in FIG. 1 is made up of a medical information system 10, a regional medical cooperation server 20, and a medical institution system 30. If the regional medical cooperation server 20 is installed at a referral source medical institution and the medical institution system 30 is installed at a referral destination medical institution, there is often a plurality of medical institution systems 30. However, the regional medical cooperation server 20 may be installed at a data center, and there may be only one medical institution system 30. Moreover, the regional medical cooperation server 20 and the medical institution system 30 are connected with each other via a network.

FIG. 2 is a view of the detailed configuration of the regional medical cooperation system according to the invention. The medical information system 10 is made up of an input/output unit 100, a control unit 101, and a medical information database 102. The regional medical cooperation server 20 is made up of a medical information system cooperation unit 201, a readmission risk calculation unit 202, a readmission risk database 203, an institution environment database 204, a referral difficulty degree calculation unit 205, a referral source screen configuration processing unit 206, a referral source input unit 207, a referral source output unit 208, and a referred patient registration database 209. The medical institution system 30 is made up of a referral destination screen configuration processing unit 301, a referral destination input unit 302, and a referral destination output unit 303. Here, the readmission risk is the risk of being readmitted to the referral source medical institution from the referral destination medical institution. Also, the referral difficulty degree indicates the degree of difficulty in patient referral.

The hardware configuration of this system will be described. FIG. 3 shows a view of the hardware configuration for realizing the regional medical cooperation system according to the invention (each component shown in FIG. 1). The medical information database 102, the readmission risk database 203, the discharge delay risk database 204 and the referred patient registration database 209 are made up of an external storage device 604 or the like, represented by an HDD (Hard Disk Drive) device. The control unit 101, the medical information system cooperation unit 201, the readmission risk calculation unit 202, the referral difficulty degree calculation unit 205, the referral source screen configuration processing unit 206 and the referral destination screen configuration processing unit 301 can realize various kinds of processing as a predetermined program is unfolded and started up in a central processing unit 603, a memory 602 or the like. The input/output unit 100, the referral source output unit 208 and the referral destination output unit 303 can be realized by a liquid crystal display 601 or a monitor utilizing a CRT (Cathode-Ray Tube) or the like. Also, an output is made on a medium such as paper. The input/output unit 100, the referral source input unit 207 and the referral destination input unit 302 can be realized by a keyboard 600, a mouse, or a pen tablet.

FIG. 4 shows a flowchart showing the outline of the regional medical cooperation system. First, a referred patient group acquired via the medical information system cooperation unit 201 is displayed on the referral source input unit 207 of the regional medical cooperation server 20 (S401). Next, as the user at the referral source medical institution selects a referred patient via the referral source input unit 207, the referral source screen configuration processing unit 206 acquires a referral destination medical institution candidate, and the referral difficulty degree, the institution information and the readmission risk of the candidate, acquired from the referral difficulty degree calculation unit 205, and displays these on the referral source output unit 208 (S402). S402, and particularly the institution information, the readmission risk and the referral difficulty degree, will be described in detail using FIGS. 8 to 15. Next, as the referral source user selects a referral destination medical institution candidate via the referral source input unit 207, the referred patient and the referral destination medical institution are registered on the referred patient registration database 209

(S403). Subsequently, in the medical institution system 30 of the referral destination medical institution, the referral destination screen configuration processing unit 301 acquires the corresponding patient information from the referred patient registration database 209 and displays this patient on the referral destination output unit 303 (S404). The user at the referral destination medical institution responds with a determination on the acceptance of the patient requested by the referral source, via the referral destination input unit 302 (S405).

Now, the flow of the operations by the user at the referral source medical institution (S401 to S403) will be described in detail. An example of display on the referral source output unit 208 is shown in FIG. 5. The screen shown in FIG. 5 is made up of a patient selection section 501, a condition setting section 502, a referral destination medical institution candidate display section 503, and a referral request button 504. In the patient selection section 501, inpatients are displayed as a referred patient group from a patient admission basic information table (described in detail with reference to FIG. 10) for managing admission and discharge information of one instance, via the medical information system cooperation unit 201. As the user selects a referred patient, a referral destination medical institution candidate that meets the setting items in the patient selection section 501 and the condition setting section 502, and the referral difficulty degree, the institution information and the readmission risk of the candidate are displayed on the cooperating hospital display section 503. In this example, the case where three institutions are displayed as referral destination medical institution candidates when a patient P0 with ischemic heart disease is selected is illustrated.

In this manner, referral destination medical institution candidates can be displayed in consideration of the readmission risk, and promotion of a regional medical cooperation structure required by increase in the number of referred patients can be realized.

Subsequently, as the user selects one of the referral destination medical institution candidates and presses the referral request button 504, the referred patient and the referral destination medical institution are registered on the referred patient registration database 209. Also, the lineup display in the referral destination medical institution candidate display section 503 may be controlled according to an item order set by the user in the condition setting section 502. For instance, in the example of FIG. 5, the case where as the user first sets the referral difficulty degree in the condition setting section 502, the lineup display is done in the referral destination medical institution candidate display section 503 according to the value of the referral difficulty degree, is illustrated. FIG. 6 shows an example of a referred patient registration table in the referred patient registration database 209. In this example, the case where an A institution is requested to accept the patient P0 with ischemic heart disease inputted in FIG. 5 is illustrated. Moreover, any patient who requires urgency may be able to be registered on the referred patient registration database 209.

By thus selecting a referral destination medical institution displayed with the readmission risk, it is possible to decide a patient referral destination medical institution in consideration of the readmission risk and promote the success of patient referral.

Next, the flow of the operations by the user at the referral destination medical institution (S404 to S405) will be described. An example of display on the referral destination output unit 303 is shown in FIG. 7. The screen shown in FIG. 7 is made up of a condition setting button 701, a condition display section 702, a referred patient display section 703, a referral approval button 704, and a referral rejection button 705. As the condition setting button 701 is pressed to set a display condition such as disease name, the display condition that is set is displayed in the condition display section 702. Moreover, a patient that matches the condition is extracted from the referred patient registration database 209 and displayed in the referred patient display section 703. As the user selects an acceptable patient from the patients displayed in the referred patient display section 703 and presses the referral approval button 704, that the patient is acceptable is transmitted to the referral source medical institution. Meanwhile, if the referral rejection button 705 is pressed, that the acceptance is difficult is transmitted. Also, the reason for rejection may be inputted with the referral rejection button 705. In this example, the case where P0 and P20 are selected and the referral approval button 704 is pressed, is illustrated.

In this manner, understanding and communication between the referral destination medical institution selected in consideration of the readmission risk and the referral source medical institution can be carried out easily Now, the institution information, the readmission risk and the referral difficulty degree in S402 of the flowchart of FIG. 4 will be described in detail using FIGS. 8 to 15. First, the institution information will be described. FIG. 8 shows an example of an institution information table and a disease basic information table stored in the institution environment database 204. The institution information table has basic information about the referral destination medical institution. In this example, the institution information table has the institution name, the postcode, the number of beds, and the number of beds available. The disease basic information table has information by institution and by disease. In this example, the disease basic information table has the number of doctors and the total number of patients accepted up until now.

Next, the readmission risk will be described. The readmission risk is the risk that the patient is readmitted to the referral source medical institution as the patient's condition worsens after the patient is transferred from the referral source medical institution to the referral destination medical institution. FIG. 9 shows a flowchart relating to the calculation of the readmission risk. First, the readmission risk calculation unit 202 calculates the readmission risk based on the information acquired from the medical information database 102 in the medical information system 10 via the medical information system cooperation unit 201 (S901). A specific calculation method will be described in the following paragraphs. Subsequently, the calculated readmission risk is stored in the readmission risk database 203 (S902). This readmission risk calculation processing is not carried out every time a patient referral is made, but is carried out by batch processing or the like in advance, for example, once a month, or the like.

Now, with respect to the method for calculating the readmission risk, a specific example of the medical information database 102 that is to be input data will be described first, and two kinds of calculation methods will be described. FIGS. 10 and 11 show an example of a patient basic information table, a patient admission basic information table and a conducted practice information table stored in the medical information database 102. The patient basic information table is a table for managing basic information of patients and has the patient code, gender, date of birth, and postcode. In this example, the case where a patient P0 is male, was born in 1950 and has a postcode 111-5214 is illustrated. The patient admission basic information table is a table for managing information about admission and discharge of one instance and has the patient code, date of admission, date of discharge, disease name, referral destination medical institution name, and readmission flag. The readmission flag of 1 indicates that readmission takes place, and 0 indicates that readmission does not take place. Also, for example, if one patient is admitted five times, five records are generated. In this example, it is shown that the patient P0 is admitted from January 10 to January 14 for ischemic heart disease, then transferred to the A institution without readmission. As for P1, it is shown that the patient is admitted twice, for hepatoma and for ischemic heart disease each, and readmitted for ischemic heart disease. The date of discharge, the referral destination medical institution name, and the readmission flag for P3 are shown as "-". This means that the patient is currently in hospital. The conducted practice information table shown in FIG. 11 is a table for managing records of medical practices conducted, and has the medical practice, date thereof, and the like. In this example, for example, the case where medical practices such as orientation and blood pressure checkup are conducted on the patient P0 is illustrated.

Next, two kinds of methods for calculating the readmission risk will be described. In both methods, the patient basic information table, the patient admission basic information table and the conducted practice information table are inputted, and the strength of the correlation between the risk of readmission, and the medical practice and patient attributes, is quantified. First, a method using the type II quantification method, which is a first calculation method, will be described. In this example, calculation is carried out, using the gender, disease name, age, referral destination medical institution and practice, as explanatory variables (variable for explaining an external criterion), and using the readmission flag as the external criterion (variable to be predicted), from the patient basic information table, the patient admission basic information table and the conducted practice information table, which are to be input data. In the readmission risk database 203, the category score (also referred to as a discriminant coefficient; a criterion for discriminating whether an element falls into one group or not) calculated as a result of the type II quantification method is stored. FIG. 12 shows a first example of a readmission risk table stored in the readmission risk database 203. In this example, the case where the category score of a category male is 0.01 is illustrated. Also, it can be understood that since the category score value of ischemic heart disease is high, it largely influences the readmission risk.

In this way, the readmission risk can be calculated and it is possible to decide a referral destination medical institution in consideration of the readmission risk.

Next, a method using association rule mining, which is a second calculation method, will be described. FIG. 13 is a flowchart relating to the method for calculating the readmission risk, in which S901 is detailed. First, using the data in the medical information database 102 as an input, association rules are generated by association rule mining (association analysis) (S9011). Next, an association rule having a readmission flag "1" in an association rule conclusion part is extracted, and all the sets of the other attributes than the readmission flag are extracted on the basis of the extracted association rule (S9012). Finally, with respect to each set of attributes extracted in S9012, the proportion of the readmission flag being "1" is calculated, using the total number of inpatients who match the set of attributes, as the denominator, and the result is the readmission risk (S9013). FIG. 14 shows a readmission risk table stored in the readmission risk database 203. This table shows the readmission risk, using the gender, practice (technique), practice (other), season, age, disease name and institution name, as explanatory variables. For example, for a patient with ischemic heart disease who is 65 years old or above and is admitted to the B institution in winter, the readmission risk is 30. Also, "-" indicates that the variable has little influence on the readmission risk.

In this method, compared with the first calculation method, only the categories that influence the readmission risk and the combinations thereof are extracted and therefore it is possible to store only effective combinations of categories in the readmission risk database 203. Thus, it is possible to realize reduction in the capacity of the database, and a higher speed of readmission risk calculation (S1504) at the time of extracting the referral difficulty degree, described next.

Finally, the referral difficulty degree will be described. The referral difficulty degree is the degree of difficulty in patient referral between the referral destination and the referral source. FIG. 15 is a flowchart relating to a method for calculating the referral difficulty degree. First, the data is acquired from the readmission risk database 203 (FIGS. 12, 14 or the like) and the institution environment database 204 (FIG. 8 or the like) (S1501). Next, a referred patient selected at the referral source input unit 207 is acquired via the referral source screen configuration processing unit 206 (S1502). Next, the patient attributes of the patient extracted in S1502 are acquired via the medical information system cooperation unit 201 (S1503). Next, the readmission risk of this patient is extracted with respect to each institution on the basis of the patient attributes extracted in S1503 and the readmission risk table extracted in S1501 (S1504). In the case of the readmission risk table shown in FIG. 12, the category score is used as the value of the readmission risk. In the case of the readmission risk table shown in FIG. 14, if there is a corresponding record, the "risk" field is used as the value of the readmission risk. If there is none, there is no influence on the readmission risk and therefore "0" can be used as the value of the readmission risk. Finally, quantitative variables are extracted or converted from the institution information extracted in S1501, the patient attributes extracted in S1503 and the readmission risk calculated in S1504, and the referral difficulty degree for each institution is calculated on the basis of these quantitative variables (S1505). It is also possible to carry out only one of the extraction and conversion. With respect to the conversion of a quantitative variable, for example, a postcode is a qualitative variable, whereas the distance calculated from the postcode of the patient and the postcode of the institution is a quantitative variable. The extraction of a quantitative variable refers to extracting a category that can be handled without carrying out processing like conversion, such as the number of beds available, as a quantitative variable. As an example of calculation of the referral difficulty degree, the distance calculated from the postcode of the patient and the postcode of the institution, the number of beds available, the total number of patients accepted (the total number of patients accepted up until now), and the readmission risk may be normalized in such a way that the average value equals the standard deviation (distribution of different quantitative variables is handled on the basis of the same standard and thus made comparable with each other), and the sum of the normalized values may be defined as the referral difficulty degree. This referral difficulty degree is calculated when "the referred patient is selected via the referral source input unit 207 in S402".

Moreover, by taking the total number of patients accepted into account in the calculation of the referral difficulty degree, it is possible to evaluate the experience point of each institution and therefore improve the quality of medical services.

With such a regional medical cooperation system, the readmission risk can be calculated on the basis of the past data and the referral destination medical institution can be thus decided. It is possible to facilitate the success of referral and realize the promotion of a regional medical cooperation structure required by increase in the number of referred patients. Moreover, by taking the total number of patients accepted into account in the calculation of the referral difficulty degree, it is possible to evaluate the experience point of each institution and therefore improve the quality of medical services.

Example 2

FIG. 16 is a second flowchart showing the outline of the regional medical cooperation system according to the invention. First, the referral source user registers a referred patient via the referral source input unit 207 (S1601). Next, with respect to a patient registered in S1601 and having a referral difficulty degree and a readmission risk equal to or below a threshold that is set in advance by the referral source user, the referral source screen configuration processing unit 206 acquires both the referral difficulty degree acquired from the referral difficulty degree calculation unit 205 and the referral destination medical institution candidate (S1602). Next, the referral source screen configuration processing unit 206 registers the acquired information of S1602 on the referred patient registration database 209 (S1603). FIG. 17 shows a referred patient registration table stored in the referred patient registration database 209. As the categories in this table, the institution name, patient name, disease name, readmission risk, geographical condition, referral difficulty degree, and referral destination acceptance availability are provided. The number of categories is larger than in FIG. 6. This is for the purpose of presenting various kinds of information to the referral destination medical institution in S1604.

Next, the referral destination screen configuration processing unit 301 acquires patient information corresponding to the own institution from the referred patient registration database 209, and displays this patient on the referral destination output unit 303 (S1604). Next, as the referral destination user inputs, via the referral destination input unit 302, a determination on acceptance of the patient requested by the referral source, the patient is registered on the referred patient registration database 209 via the referral destination screen configuration processing unit 301 (S1605). These two kinds of processing (S1604, S1605) will be described in detail using the specific example of FIG. 18. FIG. 18 shows an example of the screen displayed on the referral destination output unit 303. The screen shown in FIG. 18 is made up of a condition setting button 1801, a condition display section 1802, a referred patient display section 1803, an acceptance available button 1804, and an acceptance unavailable button 1805. As display conditions such as disease name are set via the condition setting button 1801, the display conditions that are set are displayed in the condition display section 1802. Moreover, patients who match the conditions are extracted from the referred patient registration database 209 and displayed in the referred patient display section 1803. As the referral destination user selects an acceptable patient from the patients displayed in the referred patient display section 1803 and presses the acceptance available button 1804, that the patient is acceptable is transmitted to the referral source medical institution. Meanwhile, if the acceptance unavailable button 1805 is pressed, that the acceptance is difficult is transmitted. In this example, the case where P0 and P100 are selected and where the acceptance available button 1804 is pressed is illustrated. Thus, in the referred patient registration database 209 shown in FIG. 17, "available" is shown in the referral destination acceptance availability category for P0.

Finally, the determination on acceptance acquired from the referred patient registration database 209 is displayed on the referral source output unit 208, and the referral source user approves the result of response from the referral destination user, via the referral source input unit 207 (S1606). This processing will be described in detail using the screen example of FIG. 19. The screen shown in FIG. 19 is made up of a patient selection section 1901, a candidate list 1902, a selected patient information display section 1903, a selected referral destination medical institution information display section 1904, and a referral approval button 1905. As the user selects a patient from the patient selection section 1901, referral destination medical institution candidates available for acceptance (that is, having "1" shown in the referral destination acceptance availability category) are displayed in the candidate list 1902. At the same time, detailed information of the selected patient is displayed in the selected patient information display section 1903. Subsequently, as a referral destination medical institution candidate is selected in the candidate list 1902, detailed information of the selected referral destination medical institution is displayed in the selected referral destination medical institution information display section 1904. As the user presses the referral approval button 1905 after browsing through these pieces of information, the referral to the selected referral destination medical institution is finalized and no referral is made to the other referral destination medical institution candidates that are not selected.

Now, the difference between the flowchart shown in FIG. 4 and the flowchart shown in FIG. 16 will be described. In the flowchart shown in FIG. 4, a referral request is made by the referral source medical institution with reference to the readmission risk and the referral difficulty degree in advance, and only the requested patient is displayed at the referral destination medical institution. Meanwhile, in the flowchart shown in FIG. 16, of the patients registered at the referral source medical institution, a patient corresponding only to a referral destination medical institution that satisfies a readmission risk and a referral difficulty degree below a preset threshold is displayed.

With such a regional medical cooperation system, simply by registering a patient at the referral source medical institution, it is possible to realize a referral request to a proper referral destination medical institution, in which the success of referral between the referral destination medical institution and the referral source medical institution is increased in consideration of the readmission risk. Also, since only a patient with a referral difficulty degree below a threshold is referred to the referral destination medical institution, it is possible to improve the motivations for the progress of medical skills at medical institutions, such as measures for reducing readmissions.

Example 3

FIG. 20 is a second configuration view showing the outline of the regional medical cooperation system according to the invention. A discharge delay risk calculation unit 210 and a discharge delay risk database 211 are newly added to the configuration view shown in FIG. 2, and the calculation method in the referral difficulty degree calculation unit 205 is changed. This configuration makes it possible to consider variations in the number of days spent in hospital at the time of calculating the referral difficulty degree, since the number of days spent in hospital largely varies even with the same disease, due to the patient condition or the like, for example, and consequently readmission may take place. The discharge delay risk calculation unit 210 in this configuration can realize various kinds of processing as a predetermined program is unfolded and started up in the central processing unit 603 and the memory 602 shown in FIG. 3, or the like. Also, the discharge delay risk database 211 is made up of the external storage device 604 shown in FIG. 3, or the like.

Next, FIG. 21 shows a flowchart of the discharge delay risk calculation unit 210. First, the data in the medical information database 102, particularly information of the number of days spent in hospital shown in the patient admission basic information table of FIG. 10, is acquired via the medical information system cooperation unit 201 (S2101). Next, the deviation of the number of days spent in hospital is calculated for each disease on the basis of the acquired data (S2102). Finally, the deviation calculated in S2102 is stored in the discharge delay risk database 211 as the discharge delay risk (S2103). While the deviation is calculated in this example, a distribution or coefficient of variation may be defined as the discharge delay risk.

FIG. 22 shows a second flowchart relating to a method for calculating the referral difficulty degree. The difference from the flowchart shown in FIG. 15 is that the discharge delay risk is taken into account. First, the data is acquired from the readmission risk database 203, the institution environment database 204 and the discharge delay risk database 211 (S2201). Next, a referred patient selected at the referral source input unit 207 is acquired via the referral source screen configuration processing unit 206 (S2202). Next, the patient attributes of the patient extracted in S2202 are acquired via the medical information system cooperation unit 201 (S2203). Next, the readmission risk of this patient is calculated for each institution on the basis of the patient attributes extracted in S2203 and the readmission risk table extracted in S2201 (S2204). These S2202 to S2204 are the same processing as S1502 to S1504. Next, the discharge delay risk of this patient is calculated on the basis of the patient attributes extracted in S2203 and the discharge delay risk table extracted in S2201 (S2205). This S2205 is the processing added to take the discharge delay risk into account. Finally, quantitative variables are extracted or converted from the institution information extracted in S2201, the patient attributes of the patient extracted in S2204, the readmission risk calculated in S2204 and the discharge delay risk calculated in S2205, and the referral difficulty degree is calculated for each institution on the basis of these quantitative variables (S2206). For example, the distance calculated from the postcode of the patient and the postcode of the institution, the number of beds available, the total number of patients accepted, the readmission risk and the discharge delay risk may be normalized in such a way that the average value equals the standard deviation, and the sum of the normalized values may be defined as the referral difficulty degree.

With such a regional medical cooperation system, by calculating and utilizing the discharge delay risk, it is possible to consider cases where the number of days spent in hospital largely varies even with the same disease. Thus, the referral destination medical institution can predict the scheduled date of hospital visit and the variation risk thereof, and this facilitates bed control at the referral destination medical institution. Moreover, it is possible to increase the success of patient referral between the referral source medical institution and the referral destination medical institution.

INDUSTRIAL APPLICABILITY

The invention relates to a hospital information system technique in the field of medical services and particularly useful as a technique for supporting smooth cooperation between hospitals for regional medical services.

REFERENCE SIGNS LIST

10 medical information system
100 input/output unit
101 control unit
102 medical information database
20 regional medical cooperation server
201 medical information system cooperation unit
202 readmission risk calculation unit
203 readmission risk database
204 institution environment database
205 referral difficulty degree calculation unit
206 referral source screen configuration processing unit
207 referral source input unit
208 referral source output unit
209 referred patient registration database
210 discharge delay risk calculation unit
211 discharge delay risk database
30 medical institution system
301 referral destination screen configuration processing unit
302 referral destination input unit
303 referral destination output unit
501 patient selection section
502 condition setting section
503 referral destination medical institution candidate display section
504 referral request button
600 keyboard
601 liquid crystal display
602 memory
603 central processing unit
604 external storage device
701 condition setting button
702 condition display section
703 referred patient display section
704 referral approval button
705 referral rejection button
1801 condition setting button
1802 condition display section
1803 referred patient display section
1804 acceptance available button
1805 acceptance unavailable button
1901 patient selection section
1902 candidate list
1903 selected patient information display section
1904 selected referral destination medical institution information display section
1905 referral approval button

The invention claimed is:

1. A regional medical cooperation system for supporting patient referral from a referral source medical institution to a referral destination medical institution in regional medical cooperation, the system comprising:
- a medical information database which stores medical information including patient information and information of the referral destination institution;
- a readmission risk calculation unit which calculates a readmission risk that is a risk of readmission from the referral destination medical institution to the referral source medical institution, on the basis of the medical information;
- a system referred patient information input unit which accepts an input of a first referred patient; and
- a system output unit which calculates and displays on a screen referral destination medical institution candidates, information for each candidate including at least a hospital name, a first readmission risk corresponding to the first referred patient; and a distance to each hospital by foot;
- wherein only categories that influence the readmission risk and the combinations thereof are extracted and only effective combinations of categories are stored in a readmission risk database.

2. The regional medical cooperation system according to claim 1,
- further comprising a medical institution selection input unit which accepts an input to select the referral destination medical institution, and
- comprising a medical institution system output unit which presents the first referred patient to a medical institution system of the selected referral destination medical institution.

3. The regional medical cooperation system according to claim 1, wherein
- the patient information includes a readmission flag which indicates whether readmission to the referral source medical institution is made via the referral destination medical institution or not, and
- the readmission risk calculation unit calculates a category score that is a discriminant criterion, using a type II quantification method in which the readmission flag is an external criterion that is a variable to be predicted and in which the referral destination medical institution is an explanatory variable for the external criterion, and calculates a readmission risk on the basis of the calculated category score.

4. The regional medical cooperation system according to claim 1, wherein
- the patient information includes a readmission flag which indicates whether readmission to the referral source medical institution is made via the referral destination medical institution or not, and
- the readmission risk calculation unit generates association rules by association rule mining with respect to data stored in the medical information system, extracts an association rule including the readmission flag from among the association rules, extracts sets of other attributes than the readmission flag from the association rule, and calculates a rate of readmission with respect to all inpatients that match the set of attributes, for each of the extracted sets of attributes, as a readmission risk.

5. The regional medical cooperation system according to claim 1, wherein
- the regional medical cooperation system further comprises:
- an institution information database which stores institution information of the referral destination medical institution, wherein
- the referral difficulty degree calculation unit which calculates the referral difficulty degree on the basis of the patient information, the readmission risk, and the institution information, and
- wherein the system output unit calculates and displays on a screen a referral destination medical institution, a first readmission risk and a first referral difficult degree corresponding to the first referred patient.

6. The regional medical cooperation system according to claim 5, wherein
- the referral difficulty degree calculation unit extracts quantitative variables from the patient information, the readmission risk and the institution information, normalizes the extracted quantitative variables in such a way that an average value equals a standard deviation, and calculates a sum of the normalized values as the referral difficulty degree.

7. The regional medical cooperation system according to claim 1, wherein
- the system output unit presents the first referred patient to a medical institution system output unit of a medical institution system of the referral destination medical institution if the first readmission risk is lower than a predetermined threshold.

8. The regional medical cooperation system according to claim 5, wherein
- the regional medical cooperation system comprises a discharge delay risk calculation unit which calculates a discharge delay risk that is a variation in the number of days spent in hospital by the referred patient, and
- wherein the referral difficulty degree calculation unit calculates the referral difficulty degree on the basis of the discharge delay risk, the patient information, the readmission risk and the institution information.

9. A regional medical cooperation system for supporting patient referral from a referral source medical institution to a referral destination medical institution in regional medical cooperation,
- the regional medical cooperation system including a medical information system, and a regional medical cooperation system at the referral source medical institution,
- the medical information system comprising a medical information database which stores medical information including patient information,
- the regional medical cooperation system comprising: a medical information system cooperation unit which acquires the medical information stored in the medical information database;
- a readmission risk calculation unit which calculates a readmission risk that is a risk of readmission from the referral destination medical institution to the referral source medical institution, on the basis of the medical information acquired from the medical information system cooperation unit;
- a system referred patient information input unit which accepts an input of a first referred patient; and
- a system output unit which calculates and displays on a screen referral destination medical institution candidates, information for each candidate including at least a hospital name, a first readmission risk corresponding to the first referred patient; and a distance to each hospital by foot;
- wherein only categories that influence the readmission risk and the combinations thereof are extracted and only effective combinations of categories are stored in a readmission risk database.

10. The regional medical cooperation system according to claim 9, further comprising:
- a medical institution system at the referral destination medical institution; and
- a medical institution selection input unit which accepts an input to select the referral destination medical institution, and
- comprising a medical institution system output unit which presents the first referred patient to a medical institution system of the selected referral destination medical institution.

11. The regional medical cooperation system according to claim 10, wherein
- the medical institution system of the referral destination medical institution accepts an input of acceptance availability information of the first referred patient, and the regional cooperation system acquires the acceptance availability information.

12. The regional medical cooperation system according to claim 10, wherein
- the regional cooperation system accepts an input of display condition information, and
- the system output unit displays on a screen the referral destination medical institution and the first readmission risk corresponding to the first referred patient on the basis of the display condition.

13. The regional medical cooperation system according to claim 1, wherein
- a medical institution system of the referral destination medical institution accepts an input of acceptance condition information, and determines whether presentation of the first referred patient on a medical institution system output unit of the medical institution system of the referral destination medical institution is possible or not, on the basis of the acceptance condition information.

* * * * *